(12) United States Patent
Ravishankar et al.

(10) Patent No.: US 11,699,515 B2
(45) Date of Patent: *Jul. 11, 2023

(54) SYSTEM AND METHODS FOR RECONSTRUCTING MEDICAL IMAGES USING DEEP NEURAL NETWORKS AND RECURSIVE DECIMATION OF MEASUREMENT DATA

(71) Applicant: GE Precision Healthcare LLC, Milwaukee, WI (US)

(72) Inventors: Hariharan Ravishankar, Bangalore (IN); Dattesh Dayanand Shanbhag, Bangalore (IN)

(73) Assignee: GE Precision Healthcare LLC, Milwaukee, WI (US)

( * ) Notice: Subject to any disclaimer, the term of this patent is extended or adjusted under 35 U.S.C. 154(b) by 163 days.

This patent is subject to a terminal disclaimer.

(21) Appl. No.: 17/364,544

(22) Filed: Jun. 30, 2021

(65) Prior Publication Data

US 2021/0327566 A1    Oct. 21, 2021

Related U.S. Application Data

(63) Continuation of application No. 16/691,430, filed on Nov. 21, 2019, now Pat. No. 11,133,100.

(51) Int. Cl.
*G16H 30/40* (2018.01)
*G16H 30/20* (2018.01)
(Continued)

(52) U.S. Cl.
CPC .............. *G16H 30/40* (2018.01); *A61B 5/055* (2013.01); *A61B 6/032* (2013.01); *G06N 3/045* (2023.01);
(Continued)

(58) Field of Classification Search
CPC .... A61B 5/055; A61B 6/032; G01R 33/5608; G06N 3/045; G06N 3/084; G06T 11/005;
(Continued)

(56) References Cited

U.S. PATENT DOCUMENTS

2019/0130562 A1* 5/2019 Liu .................. G06F 18/213
2019/0236817 A1   8/2019 Cheng

OTHER PUBLICATIONS

European application 20207041.3 filed Nov. 11, 2021—Extended Search Report issued Apr. 15, 2021; 9 pages.
(Continued)

*Primary Examiner* — Manuchehr Rahmjoo
(74) *Attorney, Agent, or Firm* — McCoy Russell LLP

(57) ABSTRACT

Methods and systems are provided for reconstructing images from measurement data using one or more deep neural networks according to a decimation strategy. In one embodiment, a method for reconstructing an image using measurement data comprises, receiving measurement data acquired by an imaging device, selecting a decimation strategy, producing a reconstructed image from the measurement data using the decimation strategy and one or more deep neural networks, and displaying the reconstructed image via a display device. By decimating measurement data to form one or more decimated measurement data arrays, a computational complexity of mapping the measurement data to image data may be reduced from $O(N^4)$, where N is the size of the measurement data, to $O(M^4)$, where M is the size of an individual decimated measurement data array, wherein M<N.

13 Claims, 5 Drawing Sheets

(51) Int. Cl.
- *A61B 5/055* (2006.01)
- *A61B 6/03* (2006.01)
- *G06T 7/00* (2017.01)
- *G06T 11/00* (2006.01)
- *G06N 3/045* (2023.01)

(52) U.S. Cl.
CPC .......... *G06T 7/0014* (2013.01); *G06T 11/008* (2013.01); *G16H 30/20* (2018.01); *G06T 2207/10081* (2013.01); *G06T 2207/10084* (2013.01); *G06T 2207/10088* (2013.01)

(58) Field of Classification Search
CPC ......... G06T 11/008; G06T 2207/10081; G06T 2207/10084; G06T 2207/10088; G06T 7/0014; G16H 30/20; G16H 30/40
See application file for complete search history.

(56) References Cited

OTHER PUBLICATIONS

Cooley, J. et al., "An Algorithm for the Machine Calculation of Complex Fourier Series," Mathematics of Computation, vol. 19, No. 90, Apr. 1965, 5 pages.

Duhamel, P. et al., "'Split radix' FFT algorithm," Electronics Letters, vol. 20 No. 1, Feb. 1984, Available Online Jan. 5, 1984, 4 pages.

Granger, S. et al., "Multi-scale EM-ICP: A Fast and Robust Approach for Surface Registration," Proceedings of the 7th European Conference on Computer Vision (ECCV 2002), May 28, 2002, Copenhagen, Denmark, 15 pages.

Yang, C. et al., "High-Resolution Image Inpainting using Multi-Scale Neural Patch Synthesis," Cornell University arXiv Website, Available Online at https://arxiv.org/abs/1611.09969, Available as Eady as Nov. 30, 2016, 9 pages.

Zhu, B. et al., "Image reconstruction by domain transform manifold learning," Nature, vol. 555, No. 7697, Mar. 21, 2018, 18 pages.

Eo, T. et al., "Translation of 1D Inverse Fourier Transform of K-space to an Image Based on Deep Learning for Accelerating Magnetic Resonance Imaging," Proceedings of the 21st International Conference on Medical Image Computing and Computer-Assisted Intervention, Sep. 16, 2018, Granada, Spain, 9 pages.

Moreau, A. et al., "Deep transform networks for scalable learning of MR reconstruction," Proceedings of the 27th International Society for Magnetic Resonance in Medicine (ISMRM19), May 11, 2019, Montreal, Canada, 3 pages.

Zhang, C. et al., "A divide-and-conquer strategy to overcome memory limitations of current GPUs for high resolution MRI reconstruction via a domain transform deep learning method," Proceedings of the 27th International Society for Magnetic Resonance in Medicine (ISMRM19), May 11, 2019, Montreal, Canada, 3 pages.

\* cited by examiner

SYSTEM AND METHODS FOR RECONSTRUCTING MEDICAL IMAGES USING DEEP NEURAL NETWORKS AND RECURSIVE DECIMATION OF MEASUREMENT DATA

CROSS REFERENCE TO RELATED APPLICATIONS

The present application is a continuation of U.S. Non-Provisional patent application Ser. No. 16/691,430, entitled "SYSTEM AND METHODS FOR RECONSTRUCTING MEDICAL IMAGES USING DEEP NEURAL NETWORKS AND RECURSIVE DECIMATION OF MEASUREMENT DATA", and filed on Nov. 21, 2019. The entire contents of the above-listed application are hereby incorporated by reference for all purposes.

TECHNICAL FIELD

Embodiments of the subject matter disclosed herein relate to medical imaging, and more particularly, to systems and methods for reconstructing medical images using deep neural networks.

BACKGROUND

Medical imaging systems are often used to obtain internal physiological information of a subject, such as a patient. For example, a medical imaging system may be used to obtain images of the bone structure, the brain, the heart, the lungs, and various other features of a patient. Medical imaging systems may include magnetic resonance imaging (MRI) systems, computed tomography (CT) systems, positron emission tomography (PET) systems, hybrid PET/MR systems, x-ray systems, ultrasound systems, C-arm systems, and various other imaging modalities.

Measurement data obtained by a medical imaging system (e.g., x-ray projection data in CT imaging, or k-space data in MRI), does not lend itself to visual analysis/diagnosis by a human, as the anatomical information encoded therein may be in a form which is not easily or intuitively processed by the human brain. For example, in MRI imaging, measurement data, also referred to as K-space data, comprises a two or three dimensional Fourier transform of image data, wherein each point of K-space is related to the image intensity of every pixel/voxel of a corresponding image, and therefore K-space data may be prohibitively difficult for a human mind to relate to the underlying anatomical features encoded therein. Therefore, measurement data is conventionally reconstructed to form medical images showing the anatomical structures in a form more amenable to human inspection, enabling, amongst other things, diagnosis of the acquired medical images by a human expert.

Recently, machine learning approaches have been implemented to directly map measurement data to medical image data, without relying on conventional approaches such as filtered backpropagation (FBP), homodyne algorithms, zero filling methods, dictionary learning, and, projections onto convex sets, etc. Machine learning approaches may enable more rapid medical image reconstruction, enabling shorter scan times and/or smaller doses of scanning radiation. However, the computational complexity (and therefore the time/computational resources) required in current approaches to train and implement fully connected deep neural networks capable of directly mapping measurement data to image data increases by the fourth power of the matrix size of the medical image. This "explosion of parameters" prohibits implementation of such approaches in computationally restricted environments, or for use with high-resolution or three-dimensional (3D) medical images. Therefore, it is generally desirable to explore techniques for reducing a computational complexity of medical image reconstruction using deep neural networks.

SUMMARY

In one embodiment, a method for reconstructing an image from measurement data comprises, receiving measurement data acquired by an imaging device, selecting a decimation strategy, producing a reconstructed image from the measurement data using the decimation strategy and one or more deep neural networks, and displaying the reconstructed image via a display device. In this way, measurement data may be downsampled/decimated according to a decimation strategy, thereby substantially reducing the number of parameters of the one or more deep neural networks. By decimating measurement data to form one or more decimated measurement data arrays, a computational complexity of mapping the measurement data to image data may be reduced from $O(N^4)$, where N is the size of the measurement data, to $O(M^4)$, where M is the size of an individual decimated measurement data array, where M<N, and where M may be selected independently of the image resolution.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

Figure 1:
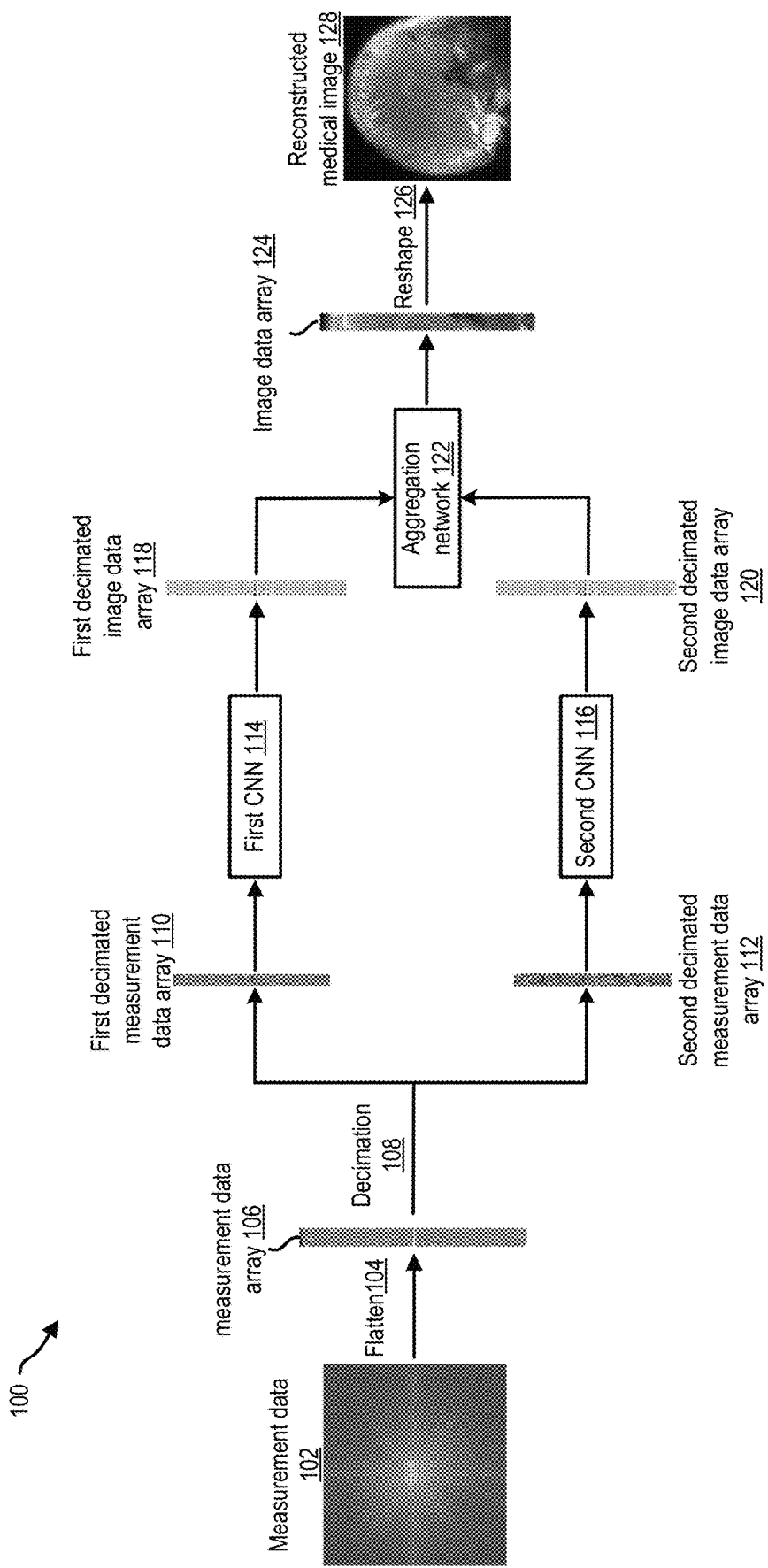
FIG. 1 shows a block diagram of an exemplary embodiment of an image reconstruction system.

The drawings illustrate specific aspects of the described systems and methods for reconstructing images using deep neural networks and a recursive decimation strategy.

Together with the following description, the drawings demonstrate and explain the structures, methods, and principles described herein. In the drawings, the size of components may be exaggerated or otherwise modified for clarity. Well-known structures, materials, or operations are not shown or described in detail to avoid obscuring aspects of the described components, systems and methods.

DETAILED DESCRIPTION

The following description relates to systems and methods for reconstructing medical images from their corresponding measurement data by recursive manifold approximations using neural networks. This approach is applicable to image reconstruction where the measurement data is related to a corresponding reconstructed image or corresponding outcome through a linear transform (e.g., Fourier transform, Radon transform, etc.). Although discussed herein in the context of medical images, it will be appreciated that the current disclosure provides for image reconstruction of substantially any imaging modality, and is not limited to medical images. Existing neural network-based methods which attempt to learn the high dimensional manifold relationship directly suffer from explosion of the number of parameters of the neural networks with increasing measurement data size, making such approaches impractical for data sizes observed in practice. The current disclosure enables neural network based image reconstruction directly from measurement data, with a reduction in the number of neural network parameters used/learned, by decimating the measurement data recursively to smaller sub-units (herein referred to as decimated measurement data arrays) which are transformed into latent manifold embeddings (herein referred to as decimated image data arrays) through a first neural network. This is followed by recursive aggregation of the decimated image data arrays using an aggregation network, to produce a reconstructed medical image. Both the first neural network and the aggregation network parameters are learned together in a joint-manner using supervised training.

The disclosed systems and methods enable a reduction in computational complexity of mapping the measurement data to image data from $O(N^4)$, for measurement data of size N×N, to $O(M^4)$, where M is the size of an individual decimated measurement data array, M<N, and where M may be selected independently of N. This reduction in parameters does not compromise the quality of image reconstruction, compared to conventional reconstruction approaches. Additionally, as the neural networks taught herein comprise substantially fewer parameters than conventional neural networks, the current approach is resistant to over-fitting, and data memorization, which are commonly cited as hindrances to adaptation of deep neural networks in image reconstruction.

The reduced computational complexity afforded by the current disclosure enables neural network based image reconstruction using measurement data on large, three-dimensional (3D) volumes generated in MRI, CT and PET clinical scanners. The current disclosure enables a dimensionality reduction of measurement data by decimating measurement data into smaller, and/or lower dimensional order, arrays, which may then be processed by one or more smaller deep neural networks. The reduced memory footprint of the one or more deep neural networks enables the approach to be implemented on hardware compromised devices, such as mobile phones, or CPU only systems. Further, the approaches of the current disclosure are applicable to a variety of imaging modalities, including magnetic resonance imaging (MRI), computed tomography (CT), positron emission tomography (PET), PET/MR, and C-Arm. The systems and methods disclosed herein may enable deployment of machine learning based image reconstruction, without the need for specialized GPU hardware, on existing computer platforms.

Figure 2:
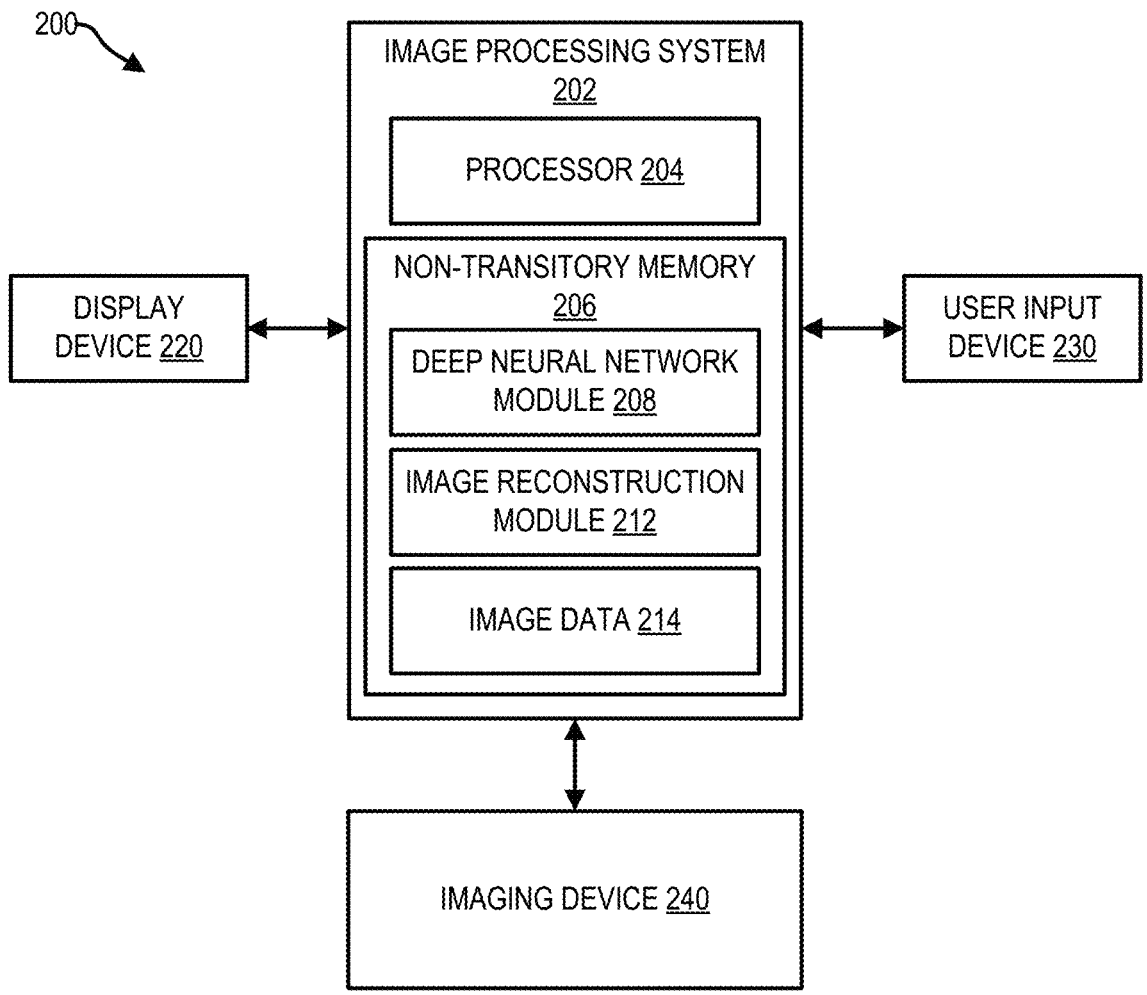
FIG. 2 is a schematic diagram illustrating an imaging system capable of implementing the image reconstruction system of FIG. 1.
Figure 3:
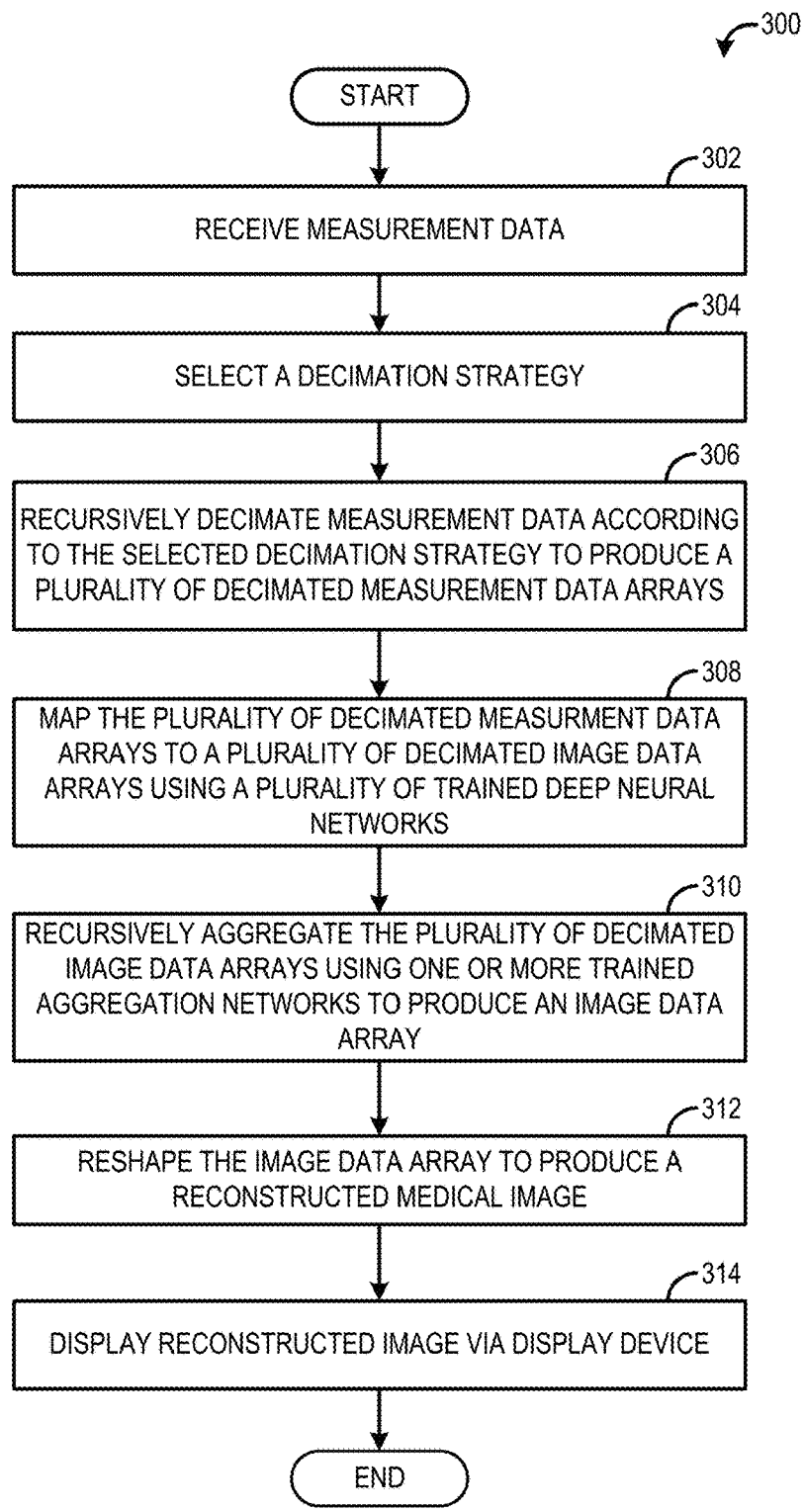
FIG. 3 is a flowchart illustrating a method for reconstructing a medical image from measurement data using one or more deep neural networks according to a decimation strategy.
Figure 4:
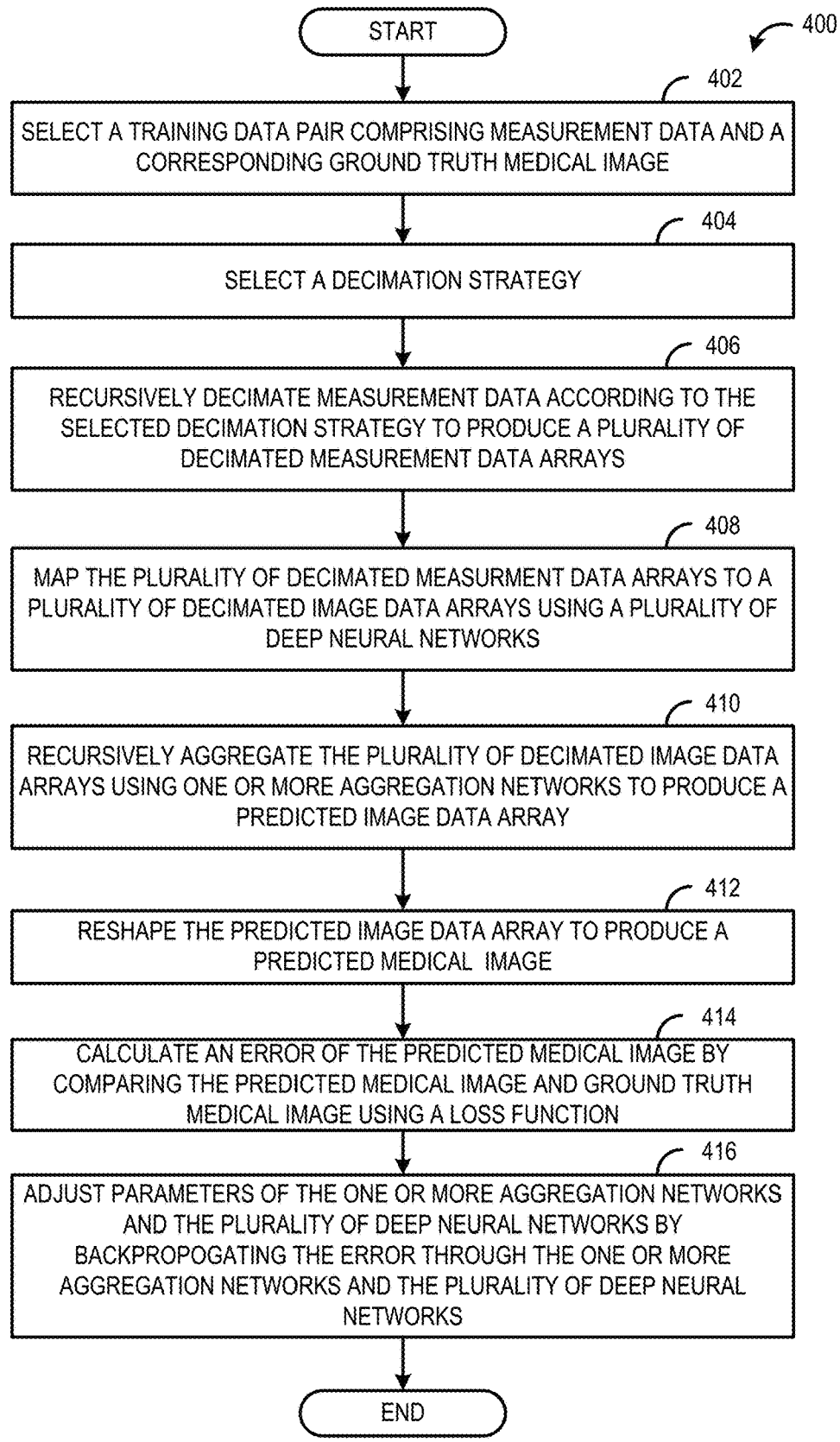
FIG. 4 is a flowchart illustrating an exemplary method for training the one or more deep neural networks of FIG. 3 using training data pairs comprising measurement data and ground truth medical images corresponding to the measurement data.
Figure 5:
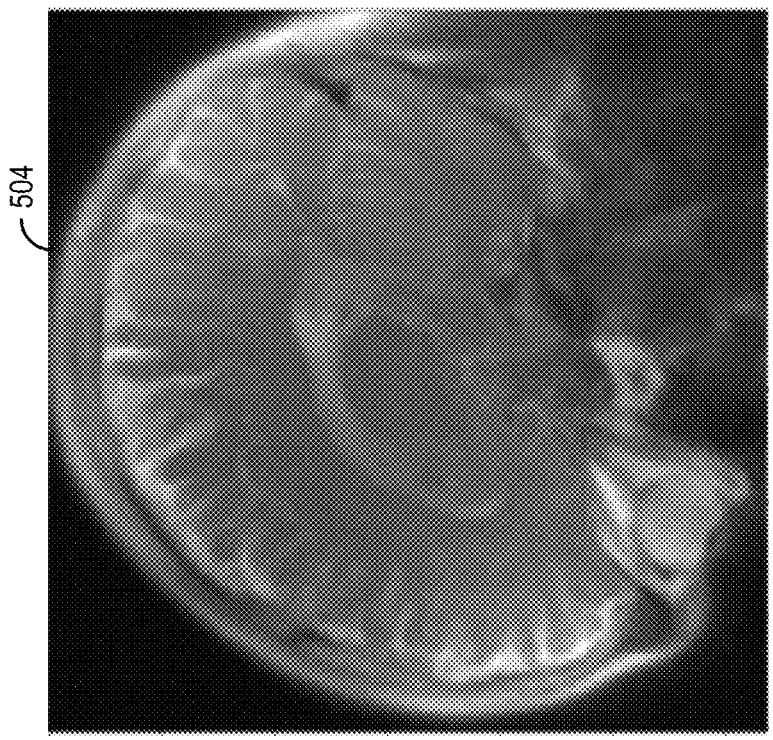
FIG. 5 shows a comparison between an image reconstructed according to an exemplary embodiment of the current disclosure, and a medical image reconstructed using a conventional approach.
Figure 5:
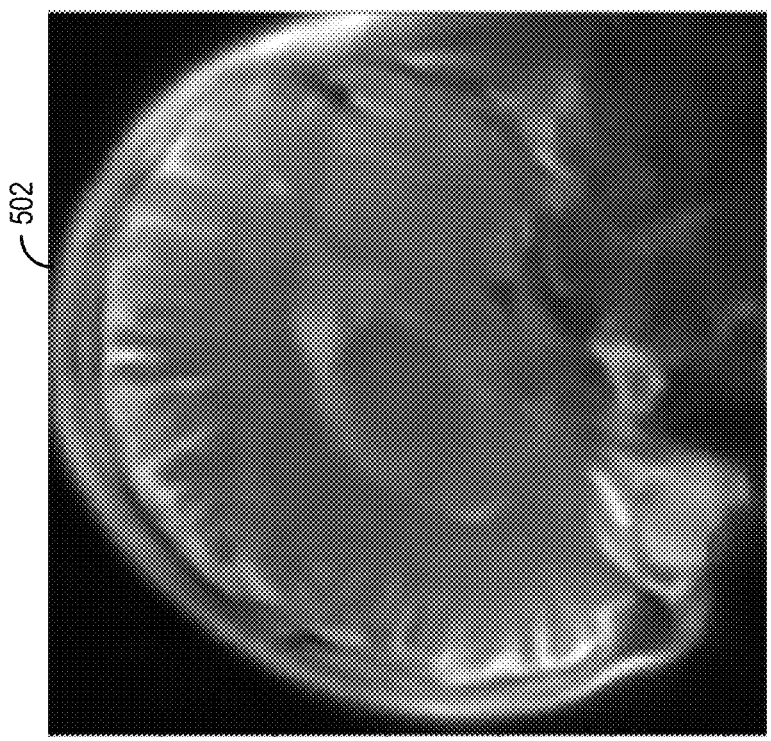

In one embodiment, the image reconstruction system 100, shown in FIG. 1, may be implemented by a medical imaging system 200, shown in FIG. 2, to reconstruct a medical image from measurement data according to one or more of the operations of method 300, shown in FIG. 3. Briefly, method 300 comprises, receiving measurement data of an anatomical region of a patient, recursively decimating the measurement data according to a decimation strategy to form a plurality of decimated measurement data arrays, mapping the plurality of decimated measurement data arrays to a plurality of decimated image data arrays using one or more trained deep neural networks, and recursively aggregating the plurality of decimated image data arrays, using one or more trained aggregation networks, to form a reconstructed medical image. FIG. 4 shows a method for training the plurality of deep neural networks and the one or more aggregation networks employed in method 300, using a joint-training approach, wherein the parameters of the deep neural networks and aggregation networks are learned together, using a same training dataset. FIG. 5 shows a comparison between a first medical image 502, which was reconstructed from measurement data using the steps of method 300, with a second medical image 504, which was produced using a conventional image reconstruction approach.

Referring to FIG. 1, an example image reconstruction system 100 is shown. Image reconstruction system 100 is one embodiment of an image reconstruction system according to the current disclosure. In particular, image reconstruction system 100 implements one example of a binary decimation strategy, wherein measurement data 102 is divided between a first decimated measurement data array 110 and a second decimated measurement data array 112. It will be appreciated that the current disclosure provides for various decimation strategies, wherein measurement data may be sampled according to one or more sampling patterns and sampling densities to produce substantially any number of decimated measurement data arrays. As an example, a trinary decimation strategy may be employed, wherein measurement data array 106 is divided/decimated into a first, second, and third decimated measurement data array.

Further, measurement data 102 comprises two-dimensional (2D) k-space data (also referred to as a Fourier plane) corresponding to reconstructed medical image 128, which comprises a 2D MRI image slice of human brain. However, it will be appreciated that the approach of the current disclosure may be used to reconstruct various images of various imaging modalities, including 3D images, CT images, PET images, etc.

Image reconstruction system 100 may receive measurement data 102 from one or more communicably coupled devices, including non-transitory data storage devices. In one embodiment, image reconstruction system 100 receives measurement data 102 from an imaging device, such as imaging device 240, discussed in more detail below, with reference to FIG. 2. In the embodiment shown in FIG. 1, measurement data 102 comprises a 128×128, 2D array of k-space data corresponding to a 2D medical image, wherein the spatial frequencies (and phases) of the intensity distribution of the 2D medical image are encoded within measurement data 102 as a Fourier plane. It will be appreciated that the current disclosure provides for reconstruction of medical images from various types of measurement data, and of various dimensional order (including 2D, 3D, etc.) wherein the measurement data is related to the medical image data via a linear transform.

Following receipt of measurement data 102 by image reconstruction system 100, measurement data 102 is reformatted as a one-dimensional (1D), measurement data array 106, via a flattening operation, as indicated by flatten 104. Flatten 104 comprises vectorization of measurement data 102, wherein the 2D arrangement of measurement data 102 is converted into an equivalent vector. In one embodiment shown by FIG. 1, measurement data array 106 comprises a 16,384 row vector of measurement data, corresponding to measurement data 102. By flattening measurement data 102, the data may be more easily decimated, as 2D, or 3D data may be flattened to an equivalent 1D representation, wherein decimation may be conducted in a more computationally efficient manner. As an example, a 2D sampling pattern may indicate a sampling frequency in both a first dimension and a second dimension, wherein, a sampling pattern of flattened image data may express the 2D sampling pattern using a single 1D sampling pattern. The computational savings may be even greater for three-dimensional (3D) measurement data, where flatten 104 may reduce the dimensionality of the measurement data from 3D to 1D, enabling a decimation strategy comprising a 1D sampling pattern to be employed.

In some embodiments, additional data may be concatenated with measurement data array 106. In one example, in MRI, multi-coil data, comprising complex k-space data, may have an associated sensitivity map. The sensitivity map data may be flattened in a manner analogous to that described with respect to measurement data 102, and the flattened sensitivity map data may be concatenated with measurement data array 106. This will provide a concatenated vector of both k-space data and sensitivity map data. In other embodiments, such as in color imaging, measurement data 102 may comprise multiple color channels (e.g., RGB color channels, or CMYK color channels, wherein each channel comprises intensity values corresponding to an associated color). The plurality of intensity values for each associated color may be separately flattened, and then concatenated, to produce measurement data array 106.

The measurement data array 106 may then be decimated, as indicated by decimation 108. Decimation 108 comprises dividing the measurement data array into two or more decimated measurement data arrays, according to a decimation strategy, wherein a decimation strategy indicates one or more of a decimation factor, a sampling pattern, and a sampling density (which may be a function of the decimation factor). Regarding the decimation factor, the decimation factor may comprise an integer or a rational fraction greater than one. The decimation factor may be used to determine a sampling rate or sampling interval/pattern. For example, if measurement data array 106 comprises a 16,384 row vector, wherein each row includes a distinct intensity value from measurement data 102, and measurement data array 106 is decimated using a decimation factor of 4, four decimated measurement data arrays will be produced, each comprising 4,096 rows of intensity values.

In the embodiment shown in FIG. 1, the measurement data array 106 is divided into a first decimated measurement data array 110, and a second decimated measurement data array 112, using a binary decimation strategy. In one embodiment, a binary decimation strategy includes a decimation factor of 2, and a homogenous sampling pattern, which may comprise apportioning each odd row of measurement data array 106 to first decimated measurement data array 110, and apportioning each even row of measurement data 106 to the second decimated measurement data array 112. In other embodiments, a heterogeneous sampling pattern may be employed, wherein the sampling pattern varies as a function position within measurement data array 106. It will be appreciated that a binary, trinary, etc., decimation strategy, producing two, three, etc., decimated measurement data arrays, may each be obtained using a plurality of sampling patterns/sampling frequencies, and the current disclosure provides for each of the plurality of sampling patterns/frequencies. As an example, although a binary decimation strategy may comprise generating a first decimated measurement data array by selecting every-other intensity value in measurement data array 106, other sampling patterns, such as selecting two consecutive intensity values of measurement data array 106, followed by not selecting the next two consecutive values of measurement data array 106, may be employed. In another example, the decimation strategy may comprise a heterogeneous sampling pattern, wherein a first sampling pattern is used for a first section of measurement data array 106, and a second sampling pattern is used for a second section of measurement data array 106, etc.

First decimated measurement data array 110, and second decimated measurement data array 112, may each comprise a same number of entries/intensity values. The sum of the entries/intensity values in first decimated measurement data array and second decimated measurement data array may equal the number of entries/intensity values in measurement data 102 and/or measurement data array 106. In particular, first decimated measurement data array 110, and second decimated measurement data array 112, each comprise 8,192 intensity values arranged into vectors of 8,192 rows.

The first decimated measurement data array 110 is received by an input layer of first network 114. In one embodiment, first network 114 comprises one or more 2D convolutional layers implemented as dense layers, avoiding iteration over rows and columns by utilizing the parallelization of convolutional layers. Each of the dense/fully connected layers may be followed by a non-linear activation, using one or more activation functions known in the art of machine learning. In one example, a dense layer/fully connected layer may be implemented as a 2D convolutional layer by setting the stride and receptive field such that each output of a current layer is mapped to each input of a following layer. The fully connected/dense layers may comprise one or more learned filters, which map the Fourier plane intensity data of first decimated measurement data array 110 to image intensity data of first decimated image data array 118.

Similarly, the second decimated measurement data array 112 is received by an input layer of second network 116. In one embodiment, second network 116 comprises one or more 2D convolutional layers implemented as dense layers, thereby avoiding iteration over rows and columns by utilizing the parallelization of convolutional layers. Each of the dense/fully connected layers may be followed by a non-linear activation, using one or more activation functions known in the art of machine learning. In one example, a dense layer/fully connected layer may be implemented as a 2D convolutional layer by setting the stride and receptive field such that each output of a previous layer is mapped to each input of a following layer. The fully connected/dense layers may comprise one or more learned filters, which map the Fourier plane intensity data of second decimated measurement data array 112 to image intensity data of second decimated image data array 120. The one or more learned filters of the one or more fully connected/dense layers of first network 114 and second network 116 may be learned via a training method, such as that discussed below with reference to FIG. 4.

First decimated image data array 118, and second decimated image data array 120, may each comprise a same number of image intensity values. In the example shown in FIG. 1, first decimated image data array 118 and second decimated image data array 120 each comprise 8,192 intensity values, corresponding to the 8,192 Fourier intensity values of first decimated measurement data array 110, and second decimated measurement data array 112, respectively.

First decimated image data array 118 and second decimated image data array 120 are both input into an input layer of aggregation network 112. In one embodiment, first decimated image data array 118 and second decimated image data array 120, are concatenated row-wise, prior to being received by aggregation network 122. Aggregation network 122 may be configured to receive multiple sources of input data. In one example, aggregation network 122 may be configured to receive image data from a same imaging modality (e.g., multi-coil MR data) or from different imaging modalities (e.g., PET/CT data).

In the embodiment shown in FIG. 1, aggregation network 112 is a 1D convolutional neural network, comprising one or more fully connected/dense layers, including one or more learned 1D convolutional filters. The 1D convolutional filters of aggregation network 122 may be learned during a training routine, such as the training routine described below, with reference to FIG. 4. The 1D fully connected/dense layers map the first decimated image data array 118 and the second decimated image data array 120, to image data array 124.

Image data array 124 comprises image intensity data, synthesized from the image intensity data of first decimated image data array 118 and second decimated image data array 120. In the example shown in FIG. 1, image data array 124 comprises a 16,384 row vector, corresponding to 16,384 image intensity values.

Image data array 124 is re-shaped to produce reconstructed medical image 128, as indicated by reshape 126. Reshape 126 comprises re-arranging the rows of image data array 124 into a matrix. In one example, reshape 126 comprises dividing image data array 124 at a plurality of pre-determined rows, to produce a plurality of columns, and re-arranging the rows into a pre-determined order, thereby producing a matrix having a number of columns equal to the number of the plurality of columns.

Reconstructed medical image 128 comprises a medical image of a patient's anatomy, corresponding to measurement data 102. In the embodiment shown in FIG. 1, reconstructed medical image 126 comprises a 128×128 pixel, 2D MR image of a patient's brain.

The image reconstruction system 100 of FIG. 1 enables rapid, efficient, and robust reconstruction of a medical image, directly from measurement data, using one or more trained deep neural networks, while reducing a computational complexity/number of learned parameters by decimating the measurement data according to a pre-determined decimation strategy.

Referring to FIG. 2, a medical imaging system 200 is shown, in accordance with an exemplary embodiment. Medical imaging system 200 comprises image processing system 202, display device 220, user input device 230, and imaging device 240. In some embodiments, at least a portion of image processing system 202 is disposed at a device (e.g., edge device, server, etc.) communicably coupled to the medical imaging system 200 via wired and/or wireless connections. In some embodiments, at least a portion of image processing system 202 is disposed at a separate device (e.g., a workstation) which can receive images from the medical imaging system 200 from a storage device which stores the images generated by the medical imaging system 200.

Image processing system 202 includes a processor 204 configured to execute machine readable instructions stored in non-transitory memory 206. Processor 204 may be single core or multi-core, and the programs executed thereon may be configured for parallel or distributed processing. In some embodiments, the processor 204 may optionally include individual components that are distributed throughout two or more devices, which may be remotely located and/or configured for coordinated processing. In some embodiments, one or more aspects of the processor 204 may be virtualized and executed by remotely-accessible networked computing devices configured in a cloud computing configuration.

Non-transitory memory 206 may store deep neural network module 208, image reconstruction module 212, and image data 214. Deep neural network module 208 may include one or more deep neural networks, comprising a plurality of weights and biases, activation functions, loss functions, and instructions for implementing the one or more deep neural networks to map measurement data to image data, and/or to map decimated image data to a single image data array. For example, deep neural network module 208 may store instructions for implementing one or more neural networks, according to one more steps of methods 300 and 400, discussed in more detail below. Deep neural network module 208 may include trained and/or untrained neural networks and may further include various data, such as training data, training routines, or parameters (e.g., weights and biases), associated with one or more neural network models stored therein. Deep neural network module 208 may include instructions for training one or more of the deep neural networks. In one embodiment, deep neural network module 208 may include gradient descent algorithms, loss functions, and rules for generating and/or filtering training data. Deep neural network module 208 may include instructions that, when executed by processor 204, cause image processing system 202 to conduct one or more of the steps of method 400, discussed in more detail below. In one example, deep neural network module 208 includes instructions for receiving training data pairs from image data 214, which comprise pairs of measurement data and corresponding ground truth medical images, for use in training one or more of the deep neural networks stored in deep neural network module 208. In some embodiments, the deep neural network module 208 is not disposed at the image processing system 202.

Deep neural network module 208 may include trained and/or untrained neural networks and may further include various deep neural network metadata pertaining to the trained and/or untrained networks. In some embodiments, the deep neural network metadata may include an indication of the training data used to train a trained deep neural network, a training method employed to train a trained deep neural network, an accuracy/validation score of a trained deep neural network, and a type of imaging modality/imaging protocol for which the trained deep neural network may be applied.

Non-transitory memory 206 may further include image reconstruction module 212, which comprises instructions for implementing one or more decimation strategies, in conjunction with one or more neural networks of deep neural network module 208, to reconstruct medical images from measurement data, according to one or more of the steps of method 300, shown in FIG. 3 below.

Non-transitory memory 206 may further store image data 214, such as measurement data or corresponding reconstructed medical images acquired by imaging device 240. The medical images stored in image data 214 may comprise MR images captured by an MRI system (in embodiments in which imaging device 240 is an MRI imaging device), CT images captured by a CT imaging system (in embodiments in which imaging device 240 is a CT imaging device), and/or one or more types of measurement data/raw imaging data. For example, image data 214 may include measurement data and corresponding ground truth medical images, which may be stored in an ordered format, such that measurement data an anatomical region of a subject is associated with a ground truth medical image of the same anatomical region of the same subject.

In some embodiments, the non-transitory memory 206 may include components disposed at two or more devices, which may be remotely located and/or configured for coordinated processing. In some embodiments, one or more aspects of the non-transitory memory 206 may include remotely-accessible networked storage devices configured in a cloud computing configuration.

Medical imaging system 200 further includes imaging device 240, which may comprise substantially any type of medical imaging device, including MRI, CT, PET, hybrid PET/MR, ultrasound, etc. Imaging device 240 may acquire measurement data of an anatomical region of a patient, wherein the measurement data may comprise a non-humanly intelligible encoding of imaging data of the anatomical region. Measurement data, and medical images reconstructed therefrom, may be stored in image data 214, or in other non-transitory storage devices communicably coupled with medical imaging system 200.

Medical imaging device 200 may further include user input device 230. User input device 230 may comprise one or more of a touchscreen, a keyboard, a mouse, a trackpad, a motion sensing camera, or other device configured to enable a user to interact with and manipulate data within image processing system 202.

Display device 220 may include one or more display devices utilizing virtually any type of technology. In some embodiments, display device 220 may comprise a computer monitor, and may display medical images, and measurement data. Display device 220 may be combined with processor 204, non-transitory memory 206, and/or user input device 230 in a shared enclosure, or may be a peripheral display device and may comprise a monitor, touchscreen, projector, or other display device known in the art, which may enable a user to view medical images reconstructed from measurement data acquired by imaging device 240, and/or interact with various data stored in non-transitory memory 206.

It should be understood that medical imaging system 200 shown in FIG. 2 is for illustration, not for limitation. Another appropriate medical imaging system may include more, fewer, or different components.

Turning to FIG. 3, an example method 300 for reconstructing medical images from measurement data using a deep neural networks and a decimation strategy is shown. Method 300 may be implemented by one or more of the systems described above. In one embodiment, medical imaging system 200 may implement method 300 to reconstruct a medical image corresponding to measurement data acquired by imaging device 240.

Method 300 begins at operation 302, wherein the medical imaging system receives measurement data. In one embodiment, the medical imaging system may acquire medical imaging data of an anatomical region of a patient using an imaging device, such as imaging device 240. In another embodiment, the medical imaging system may receive measurement data from a communicably coupled device, such as from an external imaging device connected to the medical imaging device via the Internet, local area connection, or other digital connection. In some embodiments, the measurement data received at operation 302 may comprise one of k-space data, CT sinogram data, PET sinogram data, optical imager and spectrometer (optical, infrared etc.) with Hadamard transform data as measurement data. Alternatively, in some embodiments, the measurement data could be transformed to a linear transform space prior to operation 304. In some embodiments, if the data is non-cartesian (e.g., radial or spiral trajectory), then the data may be re-gridded to a Cartesian grid before method 300 precedes to operation 304.

At operation 304, the medical imaging system selects a decimation strategy. In one embodiment, a user may select a decimation strategy using a user input device. In another embodiment, the medical imaging system may automatically select a decimation strategy based on one or more properties of the measurement data. In one embodiment, a first decimation strategy may be selected in response to the measurement data comprising 3D measurement data, and a second decimation strategy may be selected in response to the measurement data comprising 2D measurement data. In one embodiment, the medical imaging system may select a decimation strategy based on a size of the measurement data, and a pre-determined, non-zero, integer value, M, indicating an array size, wherein the decimation strategy may comprise decimating the measurement data into a plurality of decimated measurement data arrays, each of size M. In some embodiments, imaging modalities which are represented by separable linear transforms may be decimated using a same decimation strategy.

At operation 306, the medical imaging system recursively decimates the measurement data according to the decimation strategy selected at operation 304, to produce a plurality of decimated measurement data arrays. In some embodiments, the decimation strategy comprises a decimation factor, a sampling pattern, and a sampling frequency (wherein the sampling frequency may be a function of the decimation factor). In some embodiments, decimating the measurement data comprises sampling the measurement data using the indicated sampling pattern and sampling frequency, to produce a plurality of decimated measurement data arrays. In some embodiments, recursively decimating the measurement data according to the decimation strategy comprises sampling a first fraction of data from the measurement data and assigning the first fraction of data to a first decimated measurement data array, and sampling a second fraction of data from the measurement data and assigning the second fraction of data to a second decimated measurement data array. In some embodiments, the first decimated measurement data array and the second decimated measurement data array may be decimated, to produce additional decimated measurement data arrays including less data, and/or lower dimensional order data. This process may be continued until decimated measurement data arrays of a pre-determined size are obtained.

In some embodiments, a user may select a size, M, of the decimated measurement data arrays, and operation 306 may include decimating the measurement data to produce a plurality of arrays of size M, wherein M comprises an integer greater than one. In one example, measurement data may comprise a 100 row vector, and in response to a user selecting a decimated measurement data array size of 20, the medical imaging system may set a decimation factor of 5, and a sampling frequency of 0.20, and may decimate the 100 row vector to produce five decimated measurement data arrays, each comprising 20 rows.

At operation 308, the medical imaging system maps the plurality of decimated measurement data arrays to a plurality of decimated image data arrays using a plurality of trained deep neural networks. In one embodiment, mapping the plurality of decimated measurement data arrays to a plurality of decimated image data arrays comprises passing the plurality of decimated measurement data arrays through one or more fully connected/dense layers of one or more of the deep neural networks, wherein the one or more fully connected/dense layers of the one or more deep neural networks comprise one or more learned filters, learned during a training phase, as discussed below in more detail, with reference to FIG. 4.

At operation 310, the medical imaging system recursively aggregates the plurality of decimated image data arrays using one or more trained aggregation networks to produce an image data array. In some embodiments, aggregating the plurality of decimated image data arrays comprises inputting each of the plurality of decimated image data arrays into an input layer of an aggregation network. The aggregation network may then apply one or more one-dimensional (1D) convolutional filters to the plurality of decimated image data arrays to produce an image data array, wherein the image data array has a higher resolution than plurality of decimated image data arrays. In some embodiments, pairs of decimated image data arrays may be aggregated using an aggregation network, wherein a plurality of decimated image data arrays may be aggregated pairwise into larger and larger sub-units of an image data array. In an illustrative example, a first, second, third, and fourth decimated image data array may be aggregated by inputting the first and second decimated image data arrays into an aggregation network, wherein the aggregation network outputs a first partially aggregated image data array (also referred to herein as an image data array subunit). Similarly, the third and fourth decimated image data arrays may be input into the aggregation network, and mapped to a second partially aggregated image data array. The first and second partially aggregated image data arrays may then be input into the aggregation network, and mapped to the image data array. In the preceding example, the resolution of the first and second partially aggregated image data arrays is larger than the resolution of the first, second, third, or fourth decimated image data arrays, but is less than the resolution of the image data array. Aggregation of two or more decimated image data arrays may, in some embodiments, comprise aligning the decimated image data array vectors, and concatenating the data within the two or more decimated image data arrays by channel/row, to produce a channel-wise concatenated decimated image data array. The channel-wise concatenated decimated image data array may then be input into an input layer of an aggregation network, thereby preserving spatial information and providing the aggregation network with the spatial relationships between the intensity values of the two or more decimated image data arrays.

At operation 312, the medical imaging device reshapes the image data array to produce a reconstructed medical image. In some embodiments, reshaping the image data array to form the reconstructed medical image comprises re-arranging the rows of the image data array into a matrix, wherein each column of the matrix consists of an equal number of rows. In one example, operation 312 may include dividing the image data array at a plurality of pre-determined rows, to produce a plurality of columns, and re-arranging the columns according to a pre-determined order, thereby producing a matrix, depicting the image data of image data array in a humanly recognizable format.

At operation 314, the medical imaging device displays the reconstructed image to a user, via a display device.

Following operation 314, method 300 may end. In this way, method 300 may enable more computationally efficient medical image reconstruction, without sacrificing image resolution, and without increasing an amount of noise in the reconstructed image, compared to conventional approaches.

A technical effect of decimating measurement data to form one or more decimated measurement data arrays, is that a computational complexity of mapping the measurement data to image data may be reduced from $O(N^4)$, where N is the size of the measurement data, to $O(M^4)$, where M is the size of an individual decimated measurement data array, wherein M<N.

Turning to FIG. 4, an example of a training method 400, which may be executed by one or more of the systems described above, is shown. In one embodiment, method 400 may be used to train a medical image reconstruction system, such as medical image reconstruction system 100, shown in FIG. 1. In some embodiments, training method 400 may be used to train one or more of the deep neural networks used in method 300 to reconstruct a medical image from measurement data. In one embodiment, training method 400 may be used to learn one or more convolutional filters used in one or more of a plurality of convolutional neural networks used to map decimated measurement data arrays to decimated image data arrays. Method 400 enables training of both the convolutional neural networks, and the aggregation networks of a medical image reconstruction system, at substantially the same time, using a same set of training data, thereby increasing an efficiency of the training process.

Method 400 begins at operation 402, where the medical imaging system selects a training data pair comprising measurement data and a corresponding ground truth medical image, based on the current medical image reconstruction system being trained. In one example, a training data pair may be selected from a repository of training data, such as image data 214 of medical imaging system 200, based on metadata associated therewith. In some embodiments, for each imaging modality, a distinct medical image reconstruction system may be trained, thereby enabling the deep neural networks and aggregation networks of a given medical image reconstruction system to learn the manifolds relating measurement data in a particular imaging modality, to image data. In other words, the performance of a medical image reconstruction system may be enhanced by selectively training the medical image reconstruction system using training data comprising measurement data and a corresponding ground truth medical image, of a single type of imaging modality. Therefore, at operation 402, the medical imaging system may select a training data pair based on a pre-determined imaging modality for which the current image reconstruction system is to be trained. Metadata associated with the training data pair may indicate a type of imaging modality to which the training data pair is associated.

At operation 404, the medical imaging system selects a pre-determined decimation strategy based on the current medical image reconstruction system being trained. In some embodiments, for each decimation strategy, a distinct medical image reconstruction system may be trained, thereby enabling the deep neural networks and aggregation networks of a given medical image reconstruction system to learn a mapping from a particular size of decimated measurement data arrays to image data. In other words, the performance of a medical image reconstruction system may be enhanced by selectively training the medical image reconstruction system using a single decimation strategy. Therefore, at operation 404, the medical imaging system may select a decimation strategy based on the current medical image reconstruction system being trained, wherein the medical image reconstruction may include an indication of an associated decimation strategy for which the deep neural networks of the medical image reconstruction system are compatible.

At operation 406, the medical imaging system recursively decimates the measurement data according to the selected decimation strategy to produce a plurality of decimated measurement data arrays. In some embodiments, recursively decimating the measurement data according to the selected decimation strategy may include setting a decimation factor, a sampling pattern, and a sampling density (which may be a function of the decimation factor) according to the decimation strategy selected at operation 404, and producing a number of decimated measurement data arrays thereby. Decimation is discussed in more detail above, with reference to decimation 108 of FIG. 1.

At operation 408, the medical imaging system maps the plurality of decimated measurement data arrays to a plurality of decimated image data arrays using a plurality of deep neural networks of the current medical image reconstruction system, wherein the plurality of deep neural networks comprises one or more un-trained convolutional neural networks.

At operation 410, the medical imaging system recursively aggregates the plurality of decimated image data arrays using one or more aggregation networks to produce a predicted image data array, as described in more detail above, with reference to operation 310 of FIG. 3.

At operation 412, the medical imaging system reshapes the predicted image data array to produce a predicted medical image, as discussed in more detail with reference to operation 312 of FIG. 3, above.

At operation 414, the medical imaging system calculates an error of the predicted medical image by comparing the predicted medical image and the ground truth medical image using a loss function. In one embodiment, pixelwise error may be determined by inputting a pixel intensity (for one or more colors) of the predicted image and pixel intensity (for one or more colors) of a corresponding pixel of the ground truth medical image, into a loss function. Each pixelwise error may be summed, to produce a total error (herein more simply referred to as the error) of the predicted medical image.

At operation 416, the medical imaging system adjusts parameters of the one or more aggregation networks and the plurality of deep neural networks by backpropagating the error through the one or more aggregation networks and the plurality of deep neural networks using a backpropagation algorithm. In one embodiment, operation 416 comprises the image processing system adjusting the weights and biases of the one or more aggregation networks and the plurality of deep neural networks based on the error calculated at operation 414. In some embodiments, back propagation of the error may occur according to a gradient descent algorithm, wherein a gradient of the error function (a first derivative, or approximation of the first derivative) is determined for each weight and bias of the plurality of deep neural networks and the one or more aggregation networks. Each weight (and bias) of the plurality of deep neural networks and the one or more aggregation networks is then updated by adding the negative of the product of the gradient determined (or approximated) for the weight (or bias) and a predetermined step size, according to the below equation:

$$P_{i+1} = P_i - \eta \frac{\partial \text{Error}}{\partial P_i}$$

where $P_{i+1}$ is the updated parameter value, $P_i$ is the previous parameter value, $\eta$ is the step size, and $$\frac{\partial \text{Error}}{\partial P_i}$$

is the partial derivative of the error with respect to the previous parameter.

Following operation 416, method 400 may end. It will be appreciated that method 400 may be repeated until one or more conditions are met. In some embodiments, the one or more conditions may include the weights and biases of the one or more aggregation networks and the plurality of deep neural networks converging (that is, a rate of change of the parameters of the plurality of deep neural networks and one or more aggregation networks decreases to below a pre-determined threshold rate), the error determined at operation 414 decreases to below a pre-determined, non-zero, threshold (in some examples, the error may be determined using a validation dataset, distinct from the training data set).

In this way, both the plurality of deep neural networks and the one or more aggregation networks may be trained using a joint-training method, wherein a single training data set may be used to adjust parameters (e.g., filters/weights and biases) of both the plurality of deep neural networks and the one or more aggregation networks, increasing a training efficiency and reducing a duration of time required to train the medical image reconstruction system.

Turning to FIG. 5, a comparison between a medical image reconstructed using the approach of the current disclosure (first medical image 502) is compared against a medical image reconstructed using a conventional, and computationally expensive, reconstruction approach (second medical image 504). As can be seen, the first medical image 502 closely matches the anatomical structures included in the second medical image 504, and provides a comparable level of resolution.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method comprising:
   receiving measurement data acquired by an imaging device;
   flattening the measurement data;
   selecting a decimation strategy based on a size of the measurement data;
   producing a reconstructed image from the flattened measurement data using the decimation strategy and a plurality deep neural networks, where the selection is further based a size of an input layer of the plurality of deep neural networks;
   decimating the measurement data according to the decimation strategy to produce at least a first decimated measurement data array and a second decimated measurement data array;
   mapping the first decimated measurement data array to a first decimated image data array using a first deep neural network;
   mapping the second decimated measurement data array to a second decimated image data array using a second deep neural network;
   aggregating the first decimated image data array and the second decimated image data array using an aggregation network to produce an image data array;
   reshaping the image data array to produce the reconstructed image; and
   displaying the reconstructed image via a display device.

2. The method of claim 1, wherein the measurement data acquired by the measurement device comprises tomographic data related to the reconstructed image via a system transform.

3. The method of claim 1, wherein the measurement data comprises imaging measurement data, and wherein the imaging device comprises one of an MRI scanner, a CT scanner, a PET scanner, a PET/MR scanner, an optical scanner with Hadamard imaging, an optical and infrared Hadamard spectrometer, and a C-Arm scanner.

4. The method of claim 1, wherein the aggregation network comprises a one-dimensional (1D) convolutional layer.

5. The method of claim 1, wherein the first deep neural network comprises a first fully connected layer, and wherein the second deep neural network comprises a second fully connected layer.

6. The method of claim 1, wherein the decimation strategy includes a decimation factor and a sampling pattern.

7. The method of claim 6, wherein a size of each of the first decimated measurement data array and the second decimated measurement data array is determined based on the decimation factor.

8. The method of claim 1, wherein the measurement data is first measurement data, and wherein the first deep neural network, the second deep neural network, and the aggregation network, are trained by:
   selecting a training data pair comprising second measurement data and a corresponding ground truth image;
   decimating the second measurement data according to the decimation strategy to produce a plurality of decimated measurement data arrays;
   mapping the plurality of decimated measurement data arrays to a plurality of decimated image data arrays using the first deep neural network and the second deep neural network;
   aggregating the plurality of decimated image data arrays using the aggregation network to produce a predicted image data array;
   reshaping the predicted image data array to produce a predicted image;
   calculating an error of the predicted image by comparing the predicted image and the ground truth image using a loss function; and
   adjusting parameters of the first deep neural network, the second deep neural network, and the aggregation network, based on the error.

9. The method of claim 8, wherein adjusting parameters of the first deep neural network, the second deep neural network, and the aggregation network based on the error comprises:
   backpropagating the error through each layer of the aggregation network, the first deep neural network, and the second deep neural network; and
   adjusting parameters in each layer of the aggregation network, the first deep neural network, and the second deep neural network, to reduce the error.

10. An imaging system, comprising:
    a display device;
    an imaging device;
    a memory storing a plurality of trained deep neural networks, one or more aggregation networks and instructions; and
    a processor communicably coupled to the display device, the imaging device, and the memory, and when executing the instructions, configured to:
      acquire measurement data of an anatomical region of a patient using the imaging device;
      flattening the measurement data;
      select a decimation strategy;
      recursively decimate the flattened measurement data according to the decimation strategy to form a plurality of decimated measurement data arrays;
      map the plurality of decimated measurement data arrays to a plurality of decimated image data arrays using the plurality of trained deep neural networks; and
      recursively aggregate the plurality of decimated image data arrays, using a plurality of trained aggregation networks, to produce an image data array;
      reshaping the image data array to produce a reconstructed image; and
      display the reconstructed image via the display device.

11. The imaging system of claim 10, wherein the imaging device is one of an MRI scanner, a CT scanner, a PET scanner, a PET/MR scanner, an optical scanner with Hadamard imaging, an optical and infrared Hadamard spectrometer, and a C-Arm scanner.

12. The imaging system of claim 11, wherein the medical imaging device is the MRI scanner, and the measurement data comprises k-space data of the anatomical region of the patient acquired by the MRI scanner.

13. The imaging system of claim 10, wherein the processor is configured to recursively decimate the measurement data according to the decimation strategy to form the plurality of decimated measurement data arrays by sampling a first fraction of data from the measurement data and assigning the first fraction of data to a first decimated measurement data array, and sampling a second fraction of data and assigning the second fraction of data to a second decimated measurement data array.

\* \* \* \* \*